March 19, 1974 K. D. BUTTERS Plant Pat. 3,526
CHRYSANTHEMUM PLANT
Filed April 3, 1972
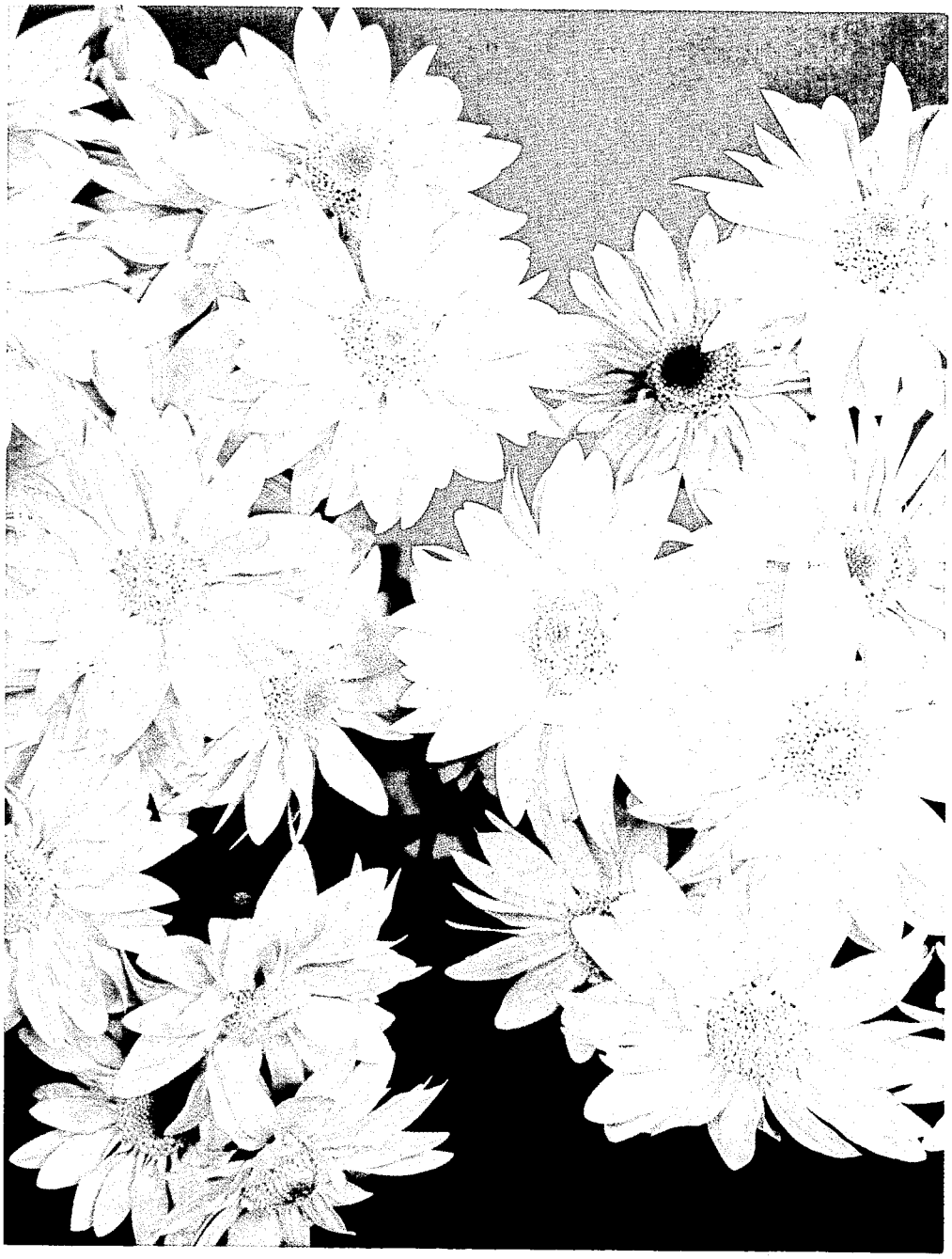

United States Patent Office

Plant Pat. 3,526

Patented Mar. 19, 1974

3,526
CHRYSANTHEMUM PLANT

Keith D. Butters, Littlehampton, England, assignor to Yoder Brothers, Inc., Barberton, Ohio

Filed Apr. 3, 1972, Ser. No. 240,859

Int. Cl. A01h *5/00*

U.S. Cl. Plt.—74 1 Claim

The present invention comprises a new and distinct cultivar of daisy form chrysanthemum plant which is a sport of the unpatented cultivar known commercially in the United States as Bronze Marble.

The new cultivar is similar in many respects to Bronze Marble, having the same characteristics of:

(1) Flower size.
(2) Daisy flower form.
(3) Plant habit.
(4) Recommended period of flowering.
(5) Foliage shape and size.

The new cultivar is distinguished from Bronze Marble, when grown under comparable conditions, by its darker, more intense bronze color.

The new cultivar was selected from a flowering block of the parent cultivar at Littlehampton, Sussex, England, and when asexually reproduced by cuttings at Littlehampton, Sussex, England, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering of the new cultivar in the northern and western United States is from April through October; in coastal California, January through December; and in Florida, December through April.

The accompanying photographic drawing shows the unique color of the new cultivar, the color being as nearly true as possible with color illustrations of this type. In the drawing, which comprises a closeup view of the flowers of the new and parent cultivars, the new cultivar appears on the left and the parent comparison cultivar appears on the right.

In the description which follows, color references are made to the Munsell Color Book, 1963 edition, and comparisons are made with the parent cultivar Bronze Marble. It should be noted that the photograph, taken in the fall of the year, does not precisely show the true colors for the new and comparison cultivar, with both flowers containing more orange tones than the flowers in actual appearance. However, the color values set forth in the specification hereinbelow are accurate and depict the true color values of both the new and parent cultivars. The color for both cultivars is somewhat lighter under high light, high temperature conditions. Where only a single value or description appears in the following description for the new cultivar, the same value or description applies also to the parent cultivar.

Botanical classification: *Chrysanthemum morifolium*

| | Gay Marble | Bronze Marble |
|---|---|---|
| Bloom: | | |
| Size | Approximately 2¾″ | |
| Fully expanded | Approximately 3¼″ | |
| Borne | In compound lateral clusters of 5 to 8 flowers | |
| Stems | Wiry | |
| Form | Daisy | |
| Permanence | 7 days | |
| Color: | | |
| Center of flower | Light green, 2, 5GY5/8 to dark yellow, 6.25Y8.5/12 | Light green, 2.5GY5/8 to dark yellow, 6.25Y8.5/12. |
| Base of petals | Yellow 7.5Y8.5/10 | Yellow, 7.5Y8.5/10. |
| Inside of petals | Red bronze, 2.5YR4/10 to light orange bronze, 7.5YR6/8 over yellow, 2.5Y8/6. | Orange bronze, 5YR6/10 over yellow, 2.5Y8.5/8. |
| Reverse of petals | Yellow, 5Y8.5/10 to buff, 7.5YR6/8 over yellow, 2.5Y8/6 | Yellow, 5Y8.5/10 to buff, 7.5YR6/8 over yellow, 2.5Y8/6. |
| Tonality from a distance | Bronze | Orange bronze. |
| Discoloration | Light orange bronze, 7.5YR6/8 over yellow, 2.5Y8/6 | Light orange bronze, 7.5YR6/8 over yellow, 2.5Y8/6. |
| Petals: | | |
| Texture | Smooth | |
| Appearance and form | Open at base, broad at mid-point, tapering to a blunt point. | |
| Arrangement | Composite ,whorled on a single receptacle | |
| Persistence | Resist shatter | |
| Fragrance | Typical chrysanthemum | |
| Reproductive organs: | | |
| Stamen, anthers | 200-250 | |
| Pollen | None to abundant (functional sterility) | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 42″ to 47″ on single stem crop given 3-5 long day weeks and 12-14 weeks total crop time as designated in the timetables of Yoder Brothers, Inc., Barberton, Ohio. | Approximately 42″ to 47″ on single stem crop given 3-5 long day weeks and 12-14 total crop time as designated in the timetables of Yoder Brothers, Inc., Barberton, Ohio. |
| Spread | None when grown single stem to moderate when pinched | |
| Foliage: | | |
| Top side | Dark green, 7.5GY3/4 | |
| Size | 5¾″ long, 3¼″ wide | |
| Quantity | Numerous | |
| Shape | Spatulate lobed | |
| Texture | Smooth | |
| Ribs & veins | Prominent | |
| Edge | Moderately indented | |
| Serration | Moderate | |
| Under side | Light green, 7.5GY5/4 | |
| Stipules | Prominent | |

I claim:

1. A new and distinct cultivar of daisy form chrysanthemum characterized particularly as to its uniqueness when compared to the parent cultivar Bronze Marble by its darker, more intense bronze color.

No references cited.

ROBERT E. BAGWILL, Primary Examiner